US010354469B2

(12) United States Patent
Ghauch et al.

(10) Patent No.: US 10,354,469 B2
(45) Date of Patent: Jul. 16, 2019

(54) SMART ANTI-COUNTERFEITING OPTICAL SYSTEM (SACOS) FOR THE DETECTION OF FRAUD USING ADVANCED SPECTROSCOPY-BASED TECHNIQUE

(71) Applicant: AMERICAN UNIVERSITY OF BEIRUT, Beirut (LB)

(72) Inventors: Antoine Ghauch, North-Chiyah (LB); Ali Ammouri, Ghobeiri (LB)

(73) Assignee: American University of Beirut, Beirut (LB)

( * ) Notice: Subject to any disclaimer, the term of this patent is extended or adjusted under 35 U.S.C. 154(b) by 0 days.

(21) Appl. No.: 15/582,295

(22) Filed: Apr. 28, 2017

(65) Prior Publication Data

US 2017/0301169 A1    Oct. 19, 2017

Related U.S. Application Data

(63) Continuation of application No. PCT/IB2015/002330, filed on Nov. 2, 2015.
(Continued)

(51) Int. Cl.
| | |
|---|---|
| *G07D 7/1205* | (2016.01) |
| *G07D 7/121* | (2016.01) |
| *G07D 7/202* | (2016.01) |
| *G01N 21/17* | (2006.01) |
| *G01N 21/47* | (2006.01) |

(Continued)

(52) U.S. Cl.
CPC .......... *G07D 7/1205* (2017.05); *G01N 21/17* (2013.01); *G01N 21/474* (2013.01); *G01N 21/64* (2013.01); *G07D 7/121* (2013.01); *G07D 7/205* (2013.01); *G01N 2021/3196* (2013.01); *G01N 2021/5957* (2013.01); *G01N 2021/6434* (2013.01)

(58) Field of Classification Search
CPC ...... G07D 7/1205; G07D 7/205; G01N 21/64; G01N 21/474; G01N 21/17; G01N 2021/3196; G01N 2021/6434; G01N 2021/5957
See application file for complete search history.

(56) References Cited

U.S. PATENT DOCUMENTS 4,577,109 A * 3/1986 Hirschfeld ........... G01N 21/255
250/461.1
4,799,756 A * 1/1989 Hirschfeld ........... G01N 21/255
250/458.1
(Continued)

FOREIGN PATENT DOCUMENTS

| CN | 202472792 | 10/2012 | ........... G07D 7/1205 |
|---|---|---|---|
| DE | 10314101 | 10/2004 | ................ G01J 3/44 |

(Continued)

OTHER PUBLICATIONS https://en.wikipedia.org/wiki/Phosphorescence.*
(Continued)

*Primary Examiner* — Mohamed K Amara
(74) *Attorney, Agent, or Firm* — J. Peter Paredes; David G. Rosenbaum; Rosenbaum IP, P.C.

(57) ABSTRACT

The SACOS apparatus solves counterfeiting issues instantaneously and develops new security features in order to improve the role that international regulatory commissions, governments, and central banks play to effectively fight counterfeiting.

14 Claims, 15 Drawing Sheets

Related U.S. Application Data

(60) Provisional application No. 62/074,396, filed on Nov. 3, 2014.

(51) Int. Cl.
*G01N 21/64* (2006.01)
*G01N 21/31* (2006.01)
*G01N 21/59* (2006.01)

(56) References Cited

U.S. PATENT DOCUMENTS

| | | | | |
|---|---|---|---|---|
| 4,994,396 A * | 2/1991 | Lefkowitz | ............ | G01N 21/643 250/459.1 |
| 5,021,665 A * | 6/1991 | Ames | ............ | F01M 11/12 250/301 |
| 5,094,819 A * | 3/1992 | Yager | ............ | G01N 21/6428 250/227.14 |
| 5,094,958 A * | 3/1992 | Klainer | ............ | G01N 21/648 250/227.23 |
| 5,096,671 A * | 3/1992 | Kane | ............ | A61B 5/14539 356/39 |
| 5,098,659 A * | 3/1992 | Yim | ............ | A61B 5/14539 422/82.06 |
| 5,173,432 A * | 12/1992 | Lefkowitz | ............ | G01N 21/6428 250/458.1 |
| 5,268,304 A * | 12/1993 | Inman | ............ | G01N 21/643 356/317 |
| 5,370,119 A * | 12/1994 | Mordon | ............ | A61B 5/0071 600/317 |
| 5,434,084 A * | 7/1995 | Burgess, Jr. | ............ | G01N 21/643 356/41 |
| 5,536,783 A * | 7/1996 | Olstein | ............ | G01N 21/6428 385/117 |
| 5,587,112 A * | 12/1996 | Kauffman | ............ | C07D 209/80 252/301.16 |
| 5,966,205 A * | 10/1999 | Jung | ............ | A61C 19/10 356/71 |
| 6,040,191 A * | 3/2000 | Grow | ............ | G01N 21/65 436/172 |
| 6,610,351 B2 * | 8/2003 | Shchegolikhin | ............ | B41M 3/14 106/31.14 |
| 6,918,482 B2 * | 7/2005 | Thierauf | ............ | G07D 7/121 194/207 |
| 7,737,417 B2 * | 6/2010 | Giering | ............ | G07D 7/1205 250/458.1 |
| 8,139,839 B2 * | 3/2012 | Giering | ............ | G07D 7/1205 194/302 |
| 9,563,798 B1 * | 2/2017 | Laser | ............ | G06K 7/10742 |
| 9,719,923 B2 * | 8/2017 | Geddes | ............ | C09K 11/025 |
| 2004/0134114 A1 | 7/2004 | Afshari | ............ | A01K 85/01 43/4.5 |
| 2005/0260764 A1 * | 11/2005 | Grigsby, Jr. | ............ | G01N 21/6428 436/172 |
| 2007/0116918 A1 * | 5/2007 | Belov | ............ | C09K 11/7731 428/64.4 |
| 2008/0259400 A1 * | 10/2008 | Hersch | ............ | B41M 3/144 358/2.1 |
| 2008/0272311 A1 * | 11/2008 | Egalon | ............ | G01N 21/6428 250/458.1 |
| 2009/0022390 A1 | 1/2009 | Yacoubian et al. | ............ | 382/135 |
| 2010/0016732 A1 * | 1/2010 | Wells | ............ | A61B 5/0059 600/476 |
| 2010/0194093 A1 * | 8/2010 | MacPherson | ............ | B42D 25/355 283/94 |
| 2010/0202726 A1 * | 8/2010 | Egalon | ............ | G01F 23/2927 385/12 |
| 2010/0328412 A1 * | 12/2010 | Watanabe | ............ | B41M 5/282 347/218 |
| 2011/0121911 A1 * | 5/2011 | Kamata | ............ | H03C 1/36 332/149 |
| 2013/0115710 A1 * | 5/2013 | Geddes | ............ | C09K 11/025 436/172 |
| 2013/0181144 A1 * | 7/2013 | Rapoport | ............ | G07D 7/12 250/459.1 |
| 2014/0034842 A1 * | 2/2014 | Kucharczyk | ............ | G01T 1/17 250/370.09 |
| 2014/0113828 A1 * | 4/2014 | Gilbert | ............ | H01L 39/126 505/100 |
| 2015/0228142 A1 * | 8/2015 | Lawandy | ............ | G01N 21/64 250/459.1 |
| 2016/0140427 A1 * | 5/2016 | Keay | ............ | G07D 7/121 235/494 |
| 2016/0215001 A1 * | 7/2016 | Trivedi | ............ | C07F 5/003 |
| 2017/0027168 A1 * | 2/2017 | Heath | ............ | A01N 25/30 |
| 2017/0205346 A1 * | 7/2017 | Urey | ............ | G01N 21/643 |
| 2017/0236034 A1 * | 8/2017 | Dolev | ............ | G06K 9/6203 705/44 |
| 2017/0299513 A1 * | 10/2017 | Geddes | ............ | A61K 8/19 |
| 2017/0309107 A1 * | 10/2017 | Sato | ............ | G07D 7/121 |
| 2017/0342319 A1 * | 11/2017 | Li | ............ | C08F 8/00 |
| 2018/0031484 A1 * | 2/2018 | Willson | ............ | C12Q 1/26 |

FOREIGN PATENT DOCUMENTS

| | | | | |
|---|---|---|---|---|
| EP | 1 832 910 | | 9/2007 | ............ G02B 26/10 |
| WO | WO 1996/24996 | | 8/1996 | ............ H04L 9/00 |
| WO | WO 2010-018353 | | 2/2010 | ............ G01N 21/64 |
| WO | WO 2010018353 A1 * | | 2/2010 | ........ G01N 21/6408 |
| WO | WO 2012/030988 | | 3/2012 | ............ G01J 3/44 |
| WO | WO 2012030988 A1 * | | 3/2012 | ............ G01J 3/0208 |

OTHER PUBLICATIONS

PCT International Search Report issued in corresponding foreign application, PCT/IB2015/002330, pp. 1-6 (May 24, 2016).
PCT International Preliminary Report on Patentability issued in corresponding foreign application, PCT/IB2015/002330, pp. 1-8 (May 18, 2017).
PCT Written Opinion issued in corresponding foreign application, PCT/IB2015/002330, pp. 1-6 (May 24, 2016).

* cited by examiner

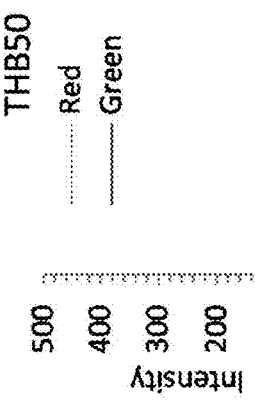
FIG. 16A
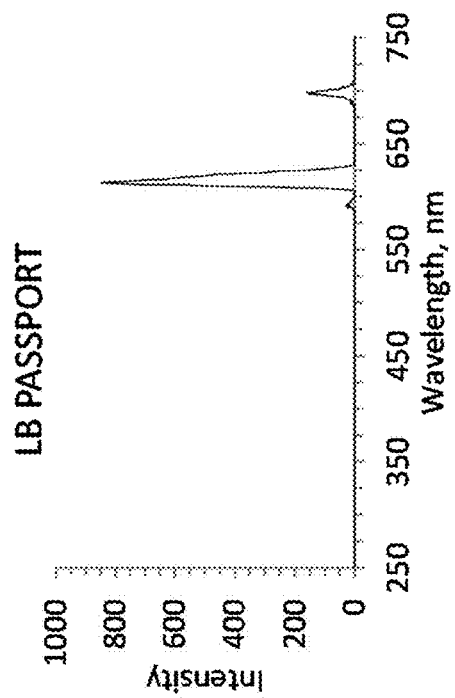
FIG. 16B
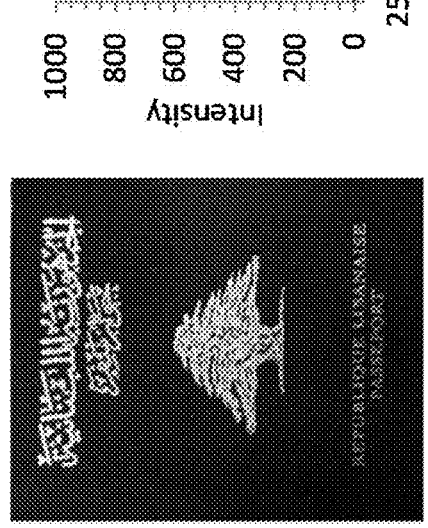
FIG. 17A
FIG. 17B

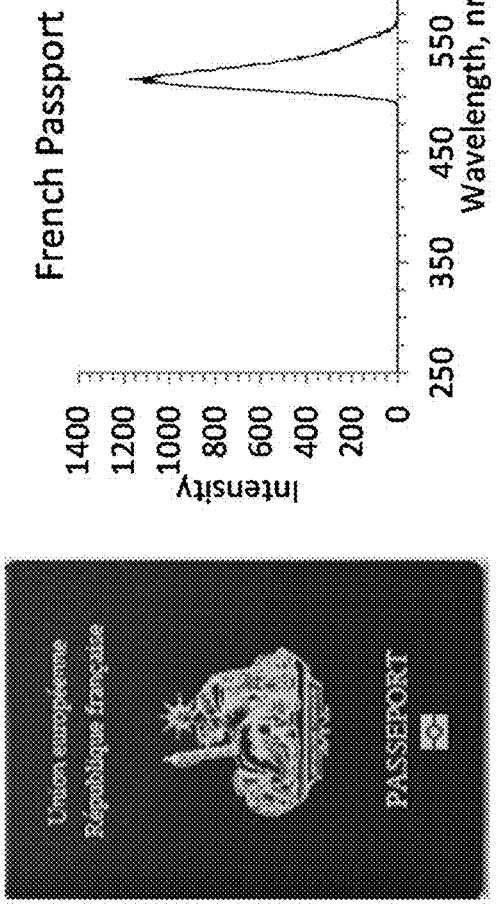
FIG. 18A
FIG. 18B
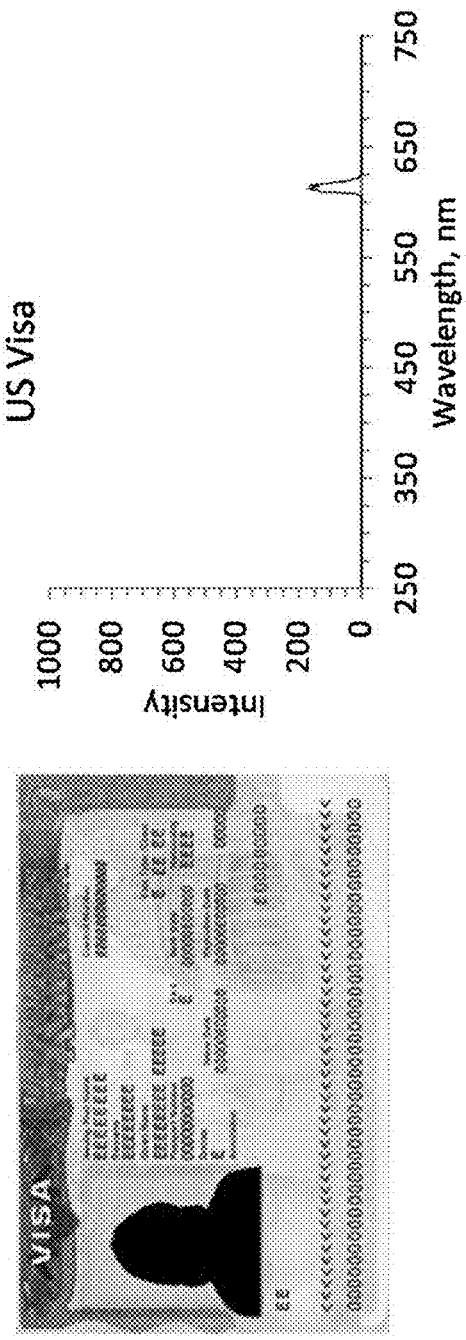
FIG. 19A
FIG. 19B

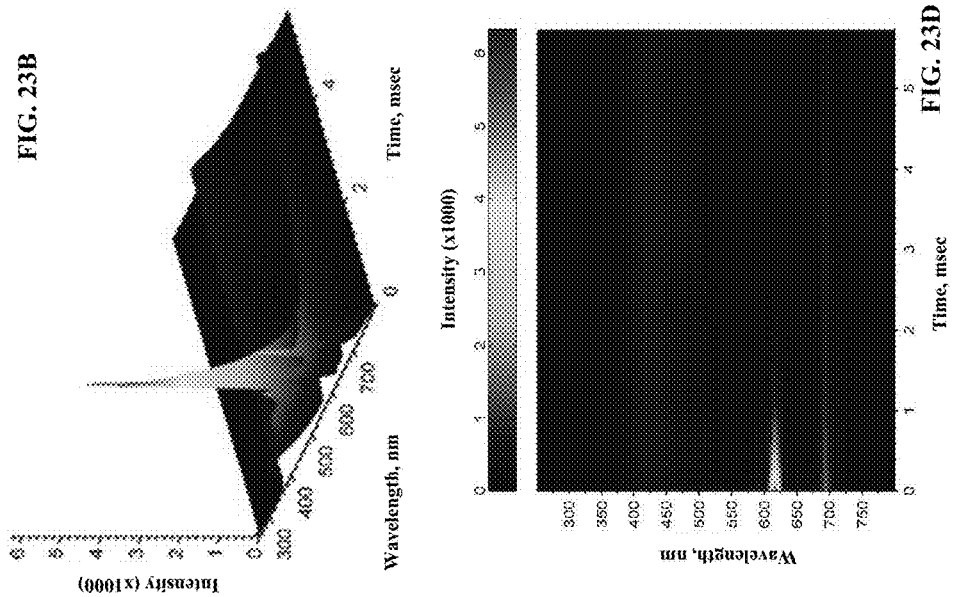
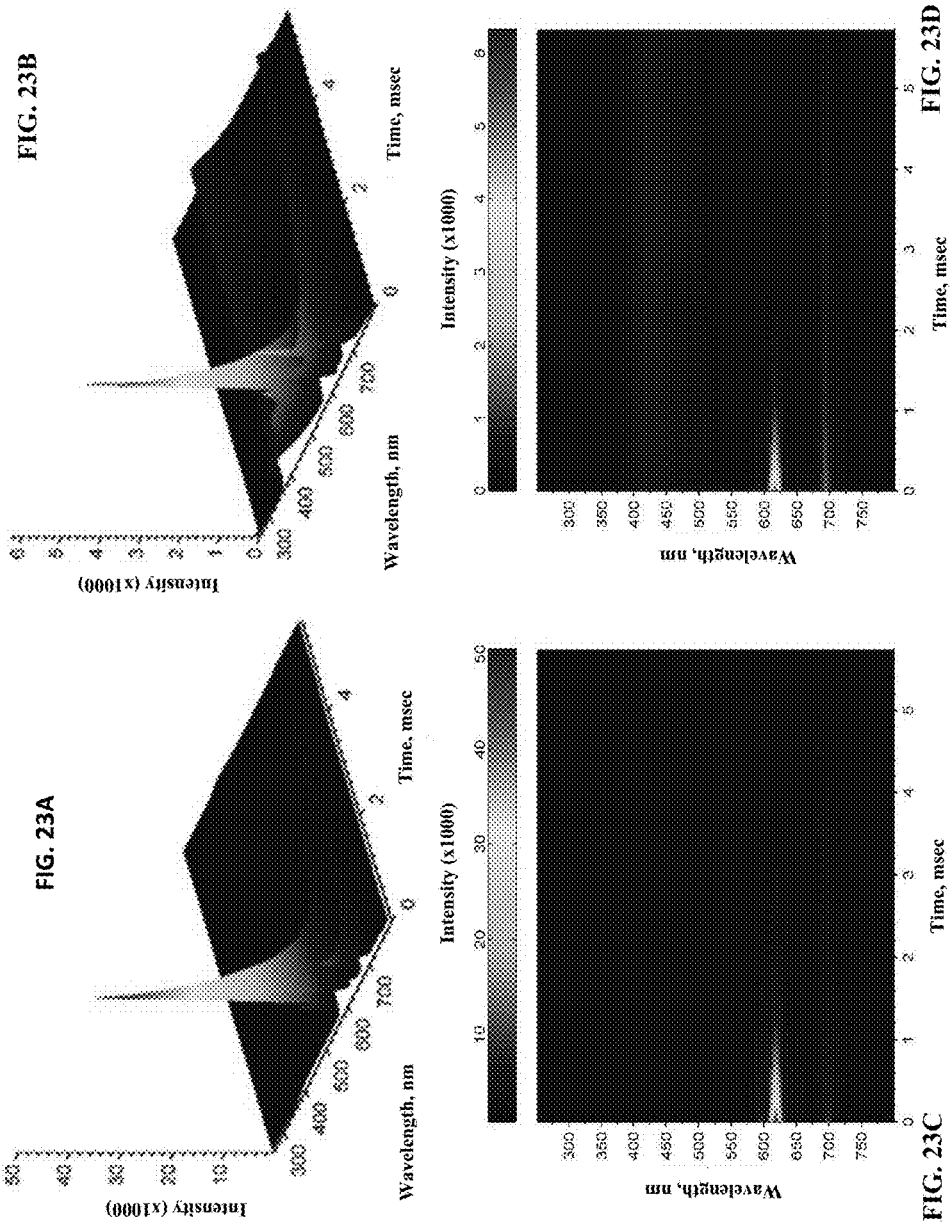
FIG. 23A
FIG. 23B
FIG. 23C
FIG. 23D

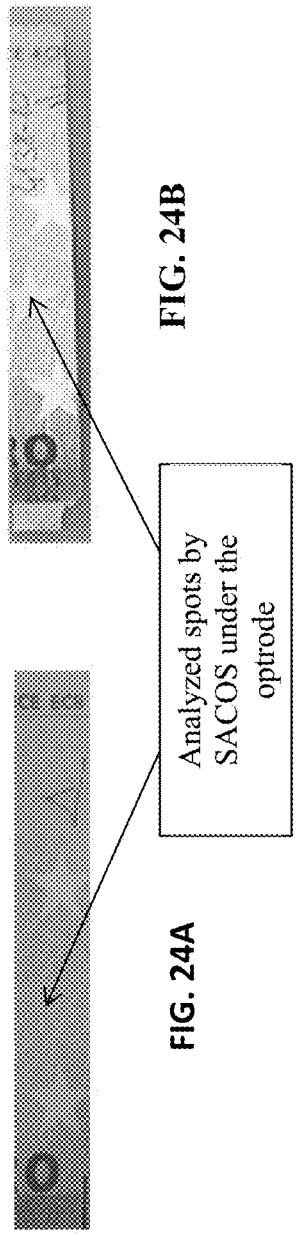

SMART ANTI-COUNTERFEITING OPTICAL SYSTEM (SACOS) FOR THE DETECTION OF FRAUD USING ADVANCED SPECTROSCOPY-BASED TECHNIQUE

CROSS-REFERENCE TO RELATED APPLICATIONS

The present application is a continuation from PCT Application Serial No. PCT/IB2015/002330, filed Nov. 2, 2015, which claims priority from U.S. Provisional Application Ser. No. 62/074,396, filed Nov. 3, 2014, each of which are incorporated herein by reference in their entireties.

BACKGROUND

The invention generally relates to anti-counterfeiting.

Analytical instrumental techniques are available for the detection of counterfeiting. All referenced arts use single wavelengths for the detection. The current solutions are: (1) Analysis of the whole piece of paper and collection of the fluorescence as an image with some special trend (that can be reproduced easily) upon continuous UV irradiation, (2) Use of bulky and very expensive machine for more accurate results. The actual solutions are not appropriate enough and 100% secure because fluorescence is only seen by naked eye on the actual machines (machines installed on borders and used by police agents) or in the laboratory where samples in questions have to be transported. One of the mainly used spectroscopic properties is the fluorescence, which can be visualized once the dye is under UV light (UV dyes). However, this technique is not at all safe to secure authenticity of documents especially that fluorescence is common to many organic molecules and that no specificity can be really followed. Fluorescence is using continuous irradiation followed by wide detection of a range of wavelengths which is known by an emission spectrum in the singlet state appearing in the UV and visible region of the electromagnetic spectrum. A quick control test of a banknote in a currency office or a passport on borders is not enough to detect falsified documents especially if fluorescence is the stand alone detection technique. The use of innovative technologies in the domain of instrumental analysis is of main importance. However results provided by such instruments should be rapidly delivered with high accuracy so as to act promptly in case of emergency.

The present invention attempts to solve these problems, as well as others.

SUMMARY OF THE INVENTION

Provided herein are systems, methods and apparatuses for a Smart Anti-Counterfeiting Optical System (SACOS).

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 16A is an image of a Thai banknote and FIG. 16B is a graph authenticated by SACOS with unique spectral fingerprints of the Thailand banknote.

FIG. 17A is an image of a Lebanese passport and FIG. 17B is a graph authenticated by SACOS with unique spectral fingerprint of the Lebanon passport.

FIG. 18A is an image of a French passport and FIG. 18B is a graph authenticated by SACOS with unique spectral fingerprint of the French passport.

FIG. 19A is an image of a United States Visa and FIG. 19B is a graph authenticated by SACOS with unique spectral fingerprint of the United States Visa.

FIG. 23A is an unique 3D phosphorescence fingerprint of an Authentic EUR200; FIG. 23B is an unique 3D phosphorescence fingerprint of an Fake EUR200; FIG. 23C is an unique 2D phosphorescence fingerprint of Authentic EUR200; and FIG. 23D is an unique 2D phosphorescence fingerprint of a Fake EUR200.

FIG. 24A is an image of an authentic EUR200 note analyzed by SACOS; and FIG. 24B is an image of a fake EUR200 note analyzed by SACOS.

DETAILED DESCRIPTION OF THE INVENTION

Figure 1:
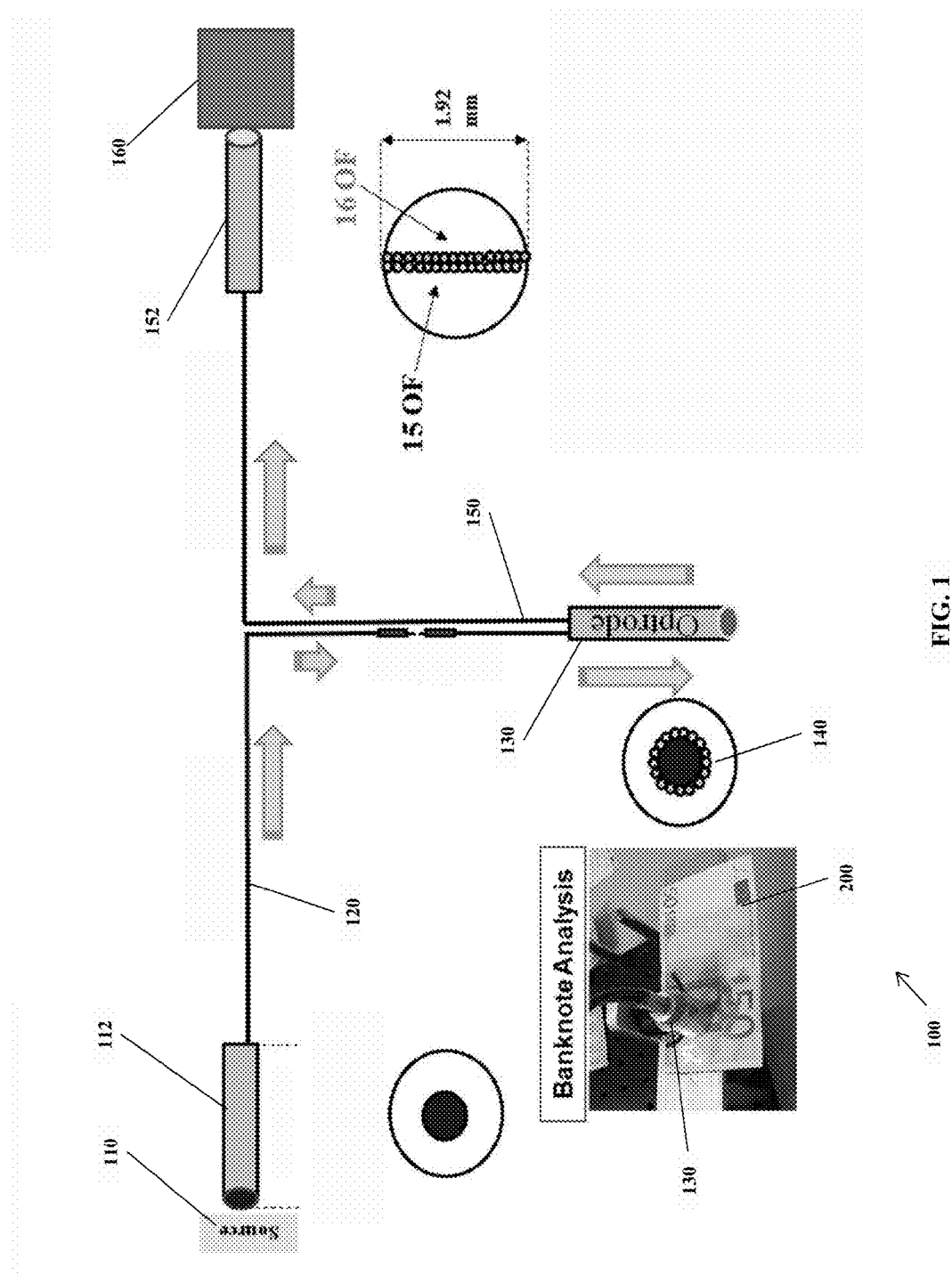
FIG. 1 is a Smart Anti-Counterfeiting Optical Sensor (SACOS) diagram showing the technical aspects addressed from the excitation source to the detector.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

A Smart Anti-Counterfeiting Optical Sensor (SACOS) is disclosed and based on spectroscopic characteristics of organic molecules used to secure banknotes and authentic documents. The SACOS system is based on the unique properties that organic dyes have with regard to their response to UV irradiation using delayed emission in the visible region of the spectrum. This non-destructive technique is applied selectively using spot-test analysis where complete cartography can explicitly show the implementation of new security features and their positioning at specific location into original documents. This SACOS technique is incorporated into a miniature and portable system in which smart software can recognize the unique signature of an organic tracer based on its emission lifetime, emission wavelength and ratios between emissive bands.

In one embodiment, the software used in SACOS allows several authentication procedures and can be easily customized to implement additional functionalities. Several schemes can be utilized to detect counterfeit documents from the software, including, but not limited the following: (1) Comparing the count peaks exceeding a predefined threshold against a predefined database; (2) A Relative scheme that includes the parameters of the (1) with an additional step of comparing the ratios of the detected peaks; (3) an Advanced scheme that uses an Artificial Neural Network (ANN) for recognizing the measured spectrum, where the Advanced Scheme can account for partially distorted spectra and thus is the most robust scheme that would reduce the false positives probability; and (4) a Life time scheme that uses the decay of the phosphorescence of the material to discriminate between the different dyes used in the banknotes.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

Generally, software include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

The Smart Anti-Counterfeiting Optical System (SACOS) is based on room temperature phosphorescence. Since the majority of banknotes and authentic papers are 100% made of cotton or cellulose, the cellulose matrix is ideal for phosphorescence enhancement. Accordingly, the SACOS system improves security features considering only papers rather than raised print, watermark, holograms, perforation, security thread, sea-through number, glossy strip, micro-printing which is more expensive to produce and control.

Phosphorescence is a specific type of photoluminescence related to fluorescence. Unlike fluorescence, a phosphorescent material does not immediately re-emit the radiation it absorbs. The slower time scales of the re-emission are associated with "forbidden" energy state transitions in quantum mechanics. As these transitions occur very slowly in certain materials, absorbed radiation may be re-emitted at a lower intensity for up to several hours after the original excitation.

Most photoluminescent events, in which a chemical substrate absorbs and then re-emits a photon of light, are fast, on the order of 10 nanoseconds. Light is absorbed and emitted at these fast time scales in cases where the energy of the photons involved matches the available energy states and allowed transitions of the substrate. In the special case of phosphorescence, the absorbed photon energy undergoes an unusual intersystem crossing into an energy state of higher spin multiplicity (see term symbol), usually a triplet state. As a result, the energy can become trapped in the triplet state with only classically "forbidden" transitions available to return to the lower energy state. These transitions, although "forbidden", will still occur in quantum mechanics but are kinetically unfavored and thus progress at significantly slower time scales. Most phosphorescent compounds are still relatively fast emitters, with triplet lifetimes on the order of milliseconds. However, some compounds have triplet lifetimes up to minutes or even hours, allowing these substances to effectively store light energy in the form of very slowly degrading excited electron states. If the phosphorescent quantum yield is high, these substances will release significant amounts of light over long time scales, creating so-called "glow-in-the-dark" materials.

$$S_0 + h\nu \rightarrow S_1 \rightarrow T_1 \rightarrow S_0 + h\nu' \qquad (1)$$

where S is a singlet and T a triplet whose subscripts denote states (0 is the ground state, and 1 the excited state). Transitions can also occur to higher energy levels, but the first excited state is denoted for simplicity.

The banknote including organic molecules, dyes, or phosphors. Phosphors are often transition metal compounds or rare earth compounds of various types. Many phosphors tend to lose efficiency gradually by several mechanisms. The activators can undergo change of valence (usually oxidation), the crystal lattice degrades, atoms—often the activators—diffuse through the material, the surface undergoes chemical reactions with the environment with consequent loss of efficiency or buildup of a layer absorbing either the exciting or the radiated energy, etc. The degradation of electroluminescent devices depends on frequency of driving current, the luminance level, and temperature; moisture impairs phosphor lifetime very noticeably as well. Harder, high-melting, water-insoluble materials display lower tendency to lose luminescence under operation. The commonly quoted parameters for phosphors are the wavelength of emission maximum (in nanometers, or alternatively color temperature in kelvins for white blends), the peak width (in nanometers at 50% of intensity), and decay time (in seconds).

Detection of counterfeiting and development of new security features dedicated to valuable documents. This detection technique will be used on Banknotes, Passports, Visas and all kind of Security Papers. It can also be used to detect molecules of forensic science interest like dopants in urine or drugs in blood.

This SACOS apparatus can identify false banknotes and falsified valuable documents instantaneously without sample destruction and in a very accurate way using a portable device of cutting edge technology. The SACOS apparatus and system uses special spectroscopic properties of organic molecules and dyes. The unusual features are the combination of the phosphorescence lifetime and the emission wavelength that can be obtained in fraction of seconds and analyzed instantaneously to discover counterfeited banknotes and non-original or fake valuable documents.

The SACOS approach is to use fundamental science by detecting emission signal not possible to detect with classical techniques. The SACOS approach includes an instrumental design to collect spectroscopic signal along the optical fiber axis and inject the signal in a smart way into a spectrometer of imaging properties and small focal plane.

The SACOS method and apparatus includes instantaneous and non-destructive analysis, analysis with high specificity, improved security features, and an accurate portable instrument. In one embodiment, SACOS method and apparatus provides feedback to the person that is selected from the group consisting of: auditory feedback (such as a voice message, alarm, buzzer, ring tone, or song); feedback via computer-generated speech; mild external electric charge or neural stimulation; periodic feedback at a selected time of the day or week; phone call; text or push notification; pre-recorded audio or video message by the person from an earlier time; television-based messages; and tactile, vibratory, or pressure-based feedback.

Figure 2:
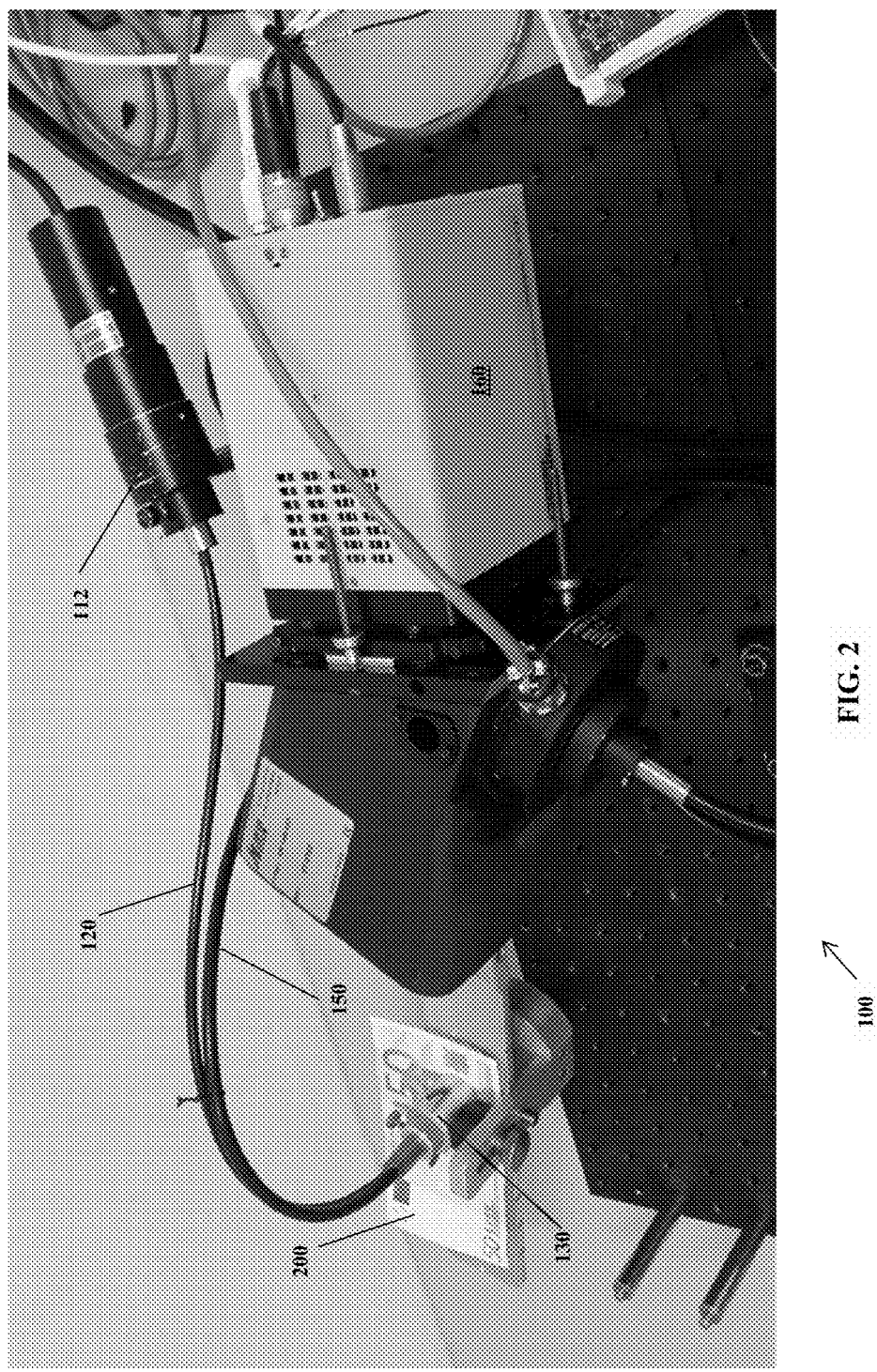
FIG. 2 is a SACOS prototype

The SACOS method and apparatus includes a sensitivity and selectivity in identifying organic tracers based on their emission lifetime. The speed in the acquisition of the signals of chemical interest may be different. Tests were carried out on banknotes, passports, visas and data were recorded. The apparatus can be of any size. A photo of this SACOS device is presented in FIG. 2.

As shown in FIG. 1, the SACOS apparatus 100 comprises an optical source 110 operably coupled to a first optical fiber 120, and a distal end of the first optical fiber 120 is operably coupled to an optrode 130 for banknote 200 analysis. In one embodiment, the optical source 110 is operably coupled to a ferrule 112, wherein the proximal end of the first optical fiber 120 is operably coupled to the ferrule 112. The optrode 130 comprises a concentric optical fiber 140. In one embodiment, the concentric optical fiber 140 includes a 1700 micron core for excitation and about 50 microns core for emission. In one embodiment, the concentric optical fiber 140 includes 2 layers of 47+46 fibers in a rectangular shape, which is guaranteed to deliver maximum signal collection.

The optrode 130 is operably coupled to a distal end of a second optical fiber 150, and the proximal end of the second optical fiber 150 is operably coupled to a detector 160. In one embodiment, the proximal end of the second optical fiber 150 is operably coupled to a ferrule 152 that is operably coupled to the detector 160. In one embodiment, the detector 160 may be a TE-charge-coupled device (CCD) array (1024×122 pixels) about 24 µm×about 24 µm pixel size, about 200-1100 nm, Integrated cooling, nominal −20° C. from ambient. In alternative embodiments, the detector may be a complementary metal oxide semiconductor (CMOS) sensor or an active-pixel sensor (APS) that is an image sensor consisting of an integrated circuit containing an array of pixel sensors, each pixel containing a photodetector and an active amplifier. In a CCD image sensor, pixels are represented by p-doped MOS capacitors. These capacitors are biased above the threshold for inversion when image acquisition begins, allowing the conversion of incoming photons into electron charges at the semiconductor-oxide interface; the CCD is then used to read out these charges.

The SACOS apparatus 100 utilizes a polychromatic excitation signal holding all wavelengths from about 190 to about 1100 nm. In one embodiment, the wavelengths from about 100 to about 2000 nm are used. The phosphorescence signal emitted from the bank note to the detector takes the form of a rectangular slit that is matched with the active zone of the CCD thus maximizing the spectrometer throughput. The optical fibers in the second optical fiber 150 are arranged linearly into two columns for maximizing throughput into the spectrometer, as shown in FIG. 1. In one embodiment, the optical fibers include about 15 optical fibers arranged in a first column and 16 optical fibers arranged in a second column. Any number of optical fibers may be arranged in the first column and second column, such as between about 2 and about 100 optical fibers.

An optode or optrode is an optical sensor device that optically measures a specific substance usually with the aid of a chemical transducer. An optode requires three components to function: a chemical that responds to an analyte, a polymer to immobilize the chemical transducer and instrumentation (optical fiber, light source, detector and other electronics). Optodes usually have the polymer matrix coated onto the tip of an optical fiber, but in the case of evanescent wave optodes the polymer is coated on a section of fiber that has been unsheathed. Optodes can apply various optical measurement schemes such as reflection, absorption, evanescent wave, luminescence (fluorescence and phosphorescences), chemiluminescence, and surface plasmon resonance.

Luminescence in solution obeys the linear Stern-Volmer relationship. Fluorescence of a molecule is quenched by specific analytes, e.g., ruthenium complexes are quenched by oxygen. When a fluorophore is immobilised within a polymer matrix a myriad of micro-environments are created. The micro-environments reflect varying diffusion co-efficients for the analyte. This leads to a non-linear relationship between the fluorescence and the quencher (analyte).

The signal (fluorescence) to oxygen ratio is not linear, and an optode is most sensitive at low oxygen concentration, i.e., the sensitivity decreases as oxygen concentration increases. The optode sensors can however work in the whole region about 0-100% oxygen saturation in water, and the calibration is done the same way as with the Clark type sensor. No oxygen is consumed and hence the sensor is stirring insensitive, but the signal will stabilize more quickly if the sensor is stirred after being put into the sample.

The SACOS apparatus is operable for data treatment and collection procedure. SACOS utilizes unique methods for matching data of standard reference material such as: (1) using of the complete wavelengths' spectrum that provides unique phosphorescence signature of the pigments and dies and (2) comparing the ratios of several signature peaks belonging to the same phosphors.

Instead of or in addition to phosphors, it is also possible to employ feature substances that are absorbing or transparent to certain wavelength ranges, e.g. to infrared light. It can likewise be provided that a phosphor is present on banknotes in different concentrations. For example, the phosphor can be present in a low concentration in the substrate of the banknotes, whereas the same feature substance is present in higher concentration in certain areas of the banknotes, e.g. in certain printed areas. If phosphors are employed whose emission wavelength changes in dependence on an applied magnetic field or whose decay behavior changes in the presence of a magnetic field, it is possible to effect an authentication for the banknotes to be checked wherein a defined magnetic field is additionally produced by a permanent magnet. This causes a light of the second wavelength to be produced when the banknotes to be checked are illuminated with the light of the first wavelength whereby the second wavelength is additionally defined by the magnetic field. If the illumination is effected with light of the first wavelength without the magnetic field, light is emitted by the feature substances with a wavelength different from the second wavelength or the decay behaviors differ.

The SACOS apparatus is able to recognize an organic molecule deposited on a solid support through a unique fingerprint. Organic molecule like some special dyes used for security features in banknotes and other secure official papers e.g. Passports, Visa, Social Security Card, Checks, driver's licenses, identification cards, and the like can be easily detected in a fraction of seconds so as to authenticate valuable documents. This SACOS instrument can also be used to control the presence of what is actually used as dyes in valuable documents but also to improve security features if using special organic molecules not actually used giving unique and even secret analytical answer.

Some special organic molecules having dyes' properties are used for their spectroscopic characteristics, such as a phosphor. The SACOS technique is based on the use of phosphorescence. Phosphorescence can be seen at room temperature (RTP) if organic molecules are deposited on a solid support minimizing vibration so as to improve radiation processes through the triplet state. This phenomenon has longer duration than fluorescence and can be detected with a delay ranging from microseconds to hundreds of milliseconds depending on the phosphor being used. Phosphorescence lifetime is specific to each molecule and can be considered in addition to the emission wavelength as a unique combination so as to improve security features. Since all valuable documents are made of papers (cellulose) or organic polymers possessing different functional groups (hydroxyl), this allows stabilization of the organic molecules incorporated into the support during the fabrication process upon irradiation. A great advantage resides here such that no additives should be used to improve RTP signals.

Figures 3A, 3B:
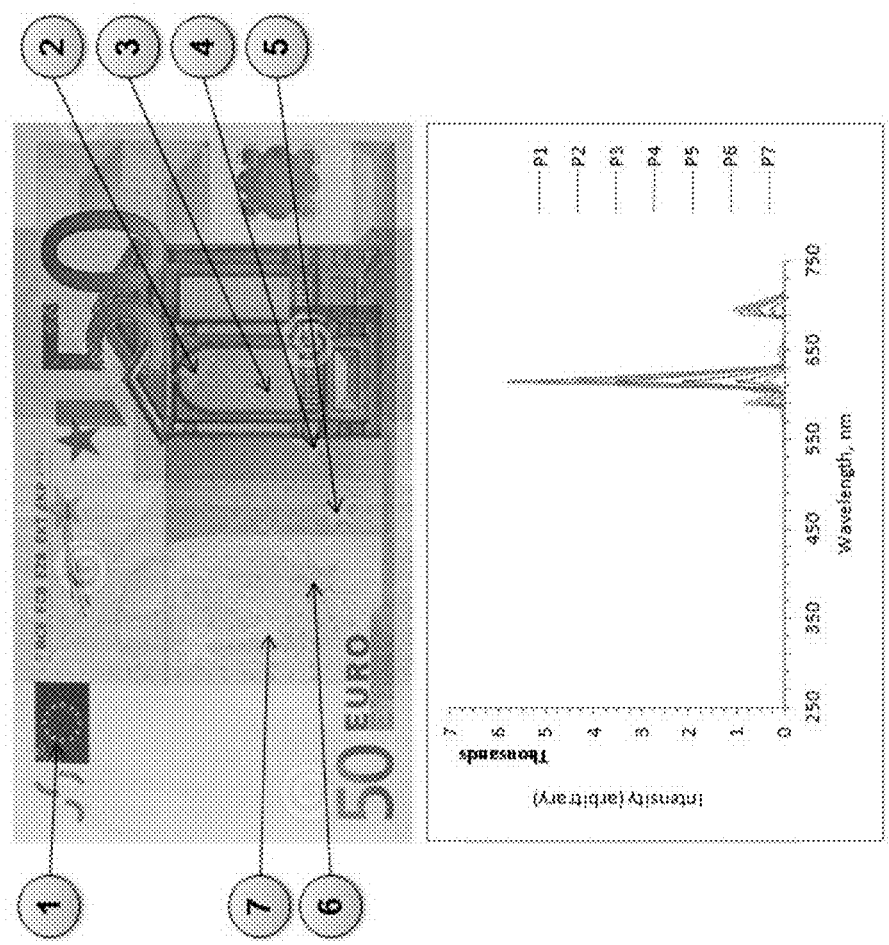
FIG. 3A is an image of a 50 Euros banknote.
FIG. 3B is a graph showing a test done on a 50 Euros banknote showing fingerprint of authentic piece. A faked banknote cannot have the same signature through SACOS.

FIG. 3B is a graph showing a test done on a 50 Euros banknote showing fingerprint of authentic piece of about 7 distinct locations of dyes in the banknote, 1, 2, 3, 4, 5, 6, and 7. Additional locations or fewer locations may be taken. P1-P7 show the distinct phosphorescence at specific wavelengths, where a faked banknote cannot have the same signature through SACOS. To further enhance the evaluation of measurements, it can be provided that there is a certain spatial arrangement of the phosphorescence on the banknote, e.g. depending on the denomination of the banknotes. Here, 7 distinct locations were taken on the banknote; however, a plurality of distinct locations of phosphorescence may be taken and measured accordingly.

Figure 4B:
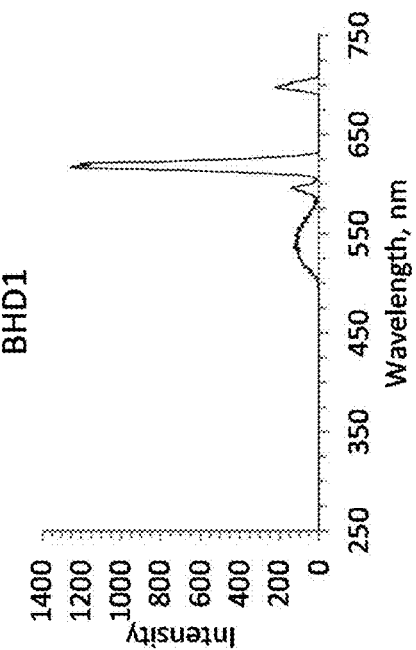
FIG. 4A is an image of a Bahraini banknote and FIG. 4B is a graph authenticated by SACOS with unique spectral fingerprints of the Bahrain banknote.
Figure 5B:
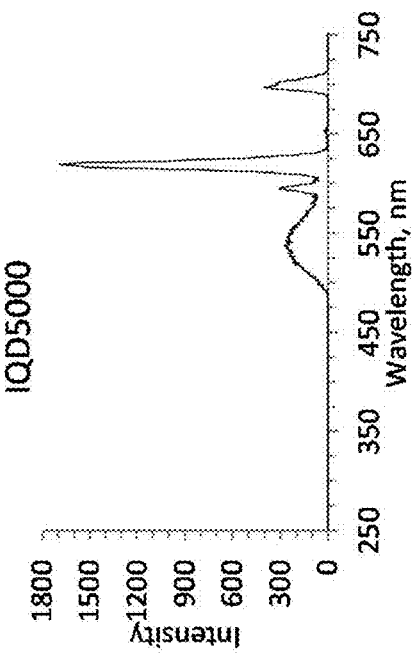
FIG. 5A is an image of an Iraqi banknote and FIG. 5B is a graph authenticated by SACOS with unique spectral fingerprints of the Iraq banknote.
Figure 4A:
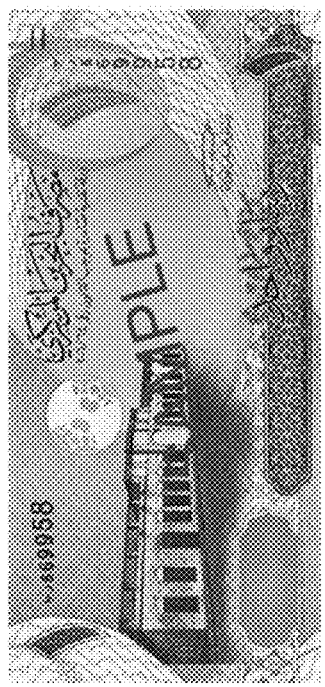
Figure 5A:
Figure 6B:
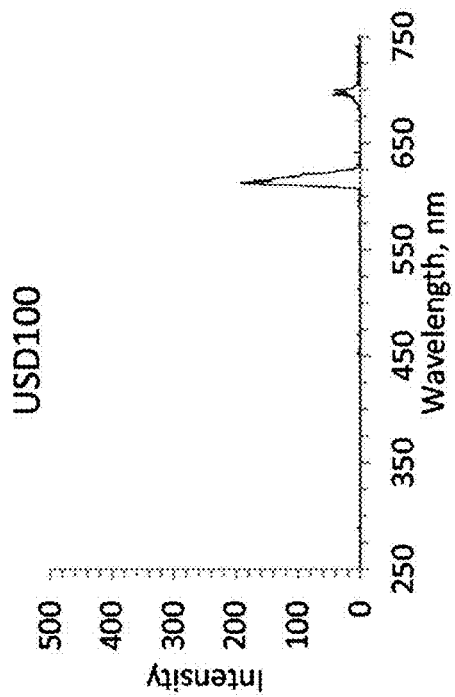
FIG. 6A is an image of a Qatari banknote and FIG. 6B is a graph authenticated by SACOS with unique spectral fingerprints of the Qatar banknote.
Figure 7B:
FIG. 7A is an image of a United States banknote and FIG. 7B is a graph authenticated by SACOS with unique spectral fingerprints of the United States banknote.
Figure 6A:
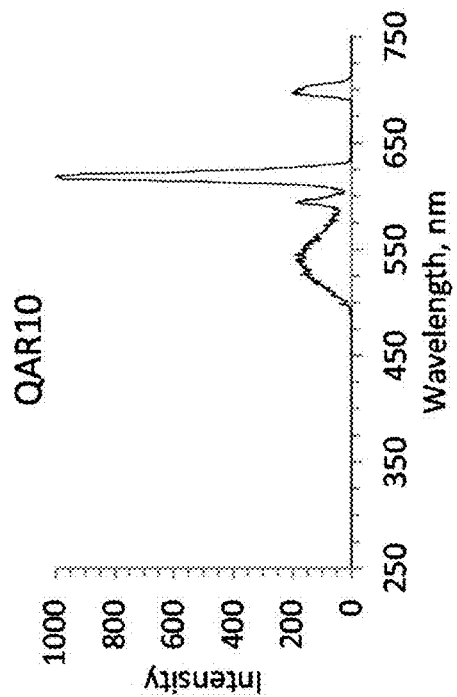
Figure 7A:
Figure 8B:
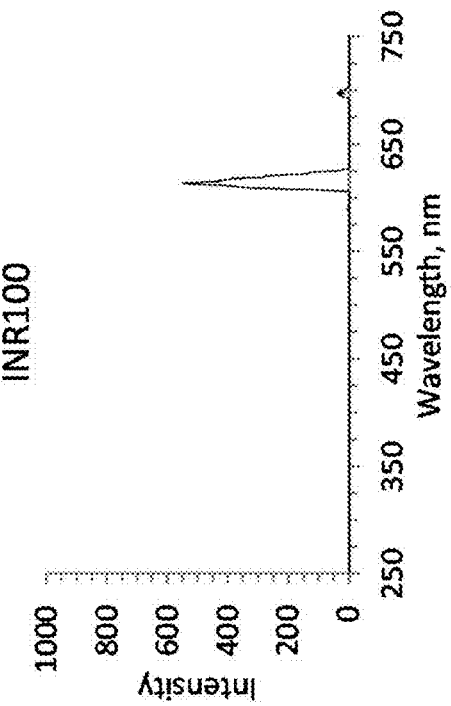
FIG. 8A is an image of a Great Britain banknote and FIG. 8B is a graph authenticated by SACOS with unique spectral fingerprints of the Great Britain banknote.
Figure 8A:
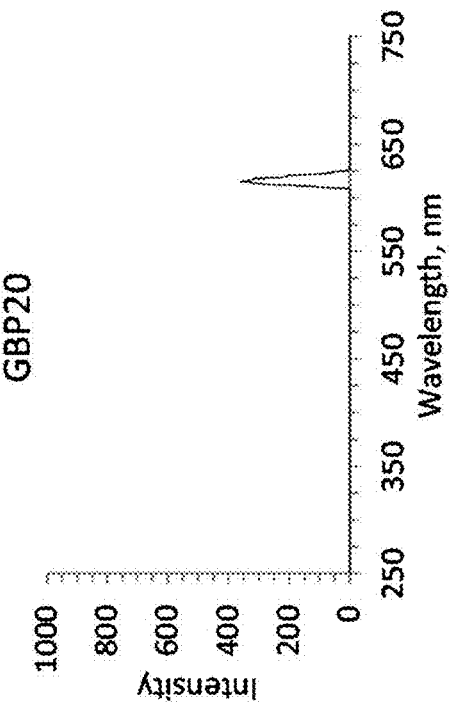
Figure 9B:
FIG. 9A is an image of an Indian banknote and FIG. 9B is a graph authenticated by SACOS with unique spectral fingerprints of the Indian banknote.
Figure 9A:
Figure 10A:
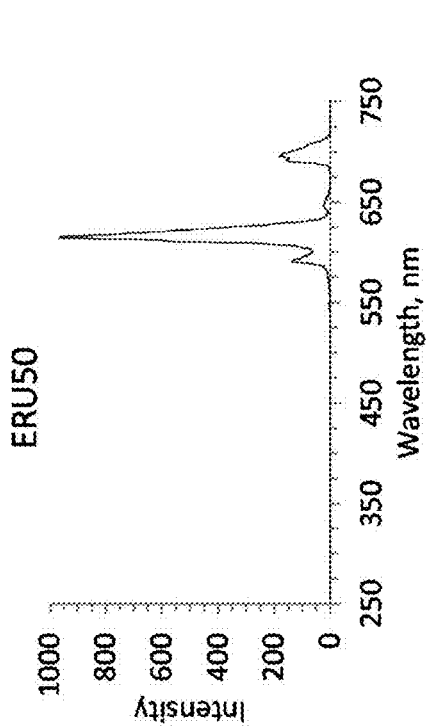
FIG. 10A is an image of a Euro banknote and FIG. 10B is a graph authenticated by SACOS with unique spectral fingerprints of the Euro banknote.
Figure 10B:
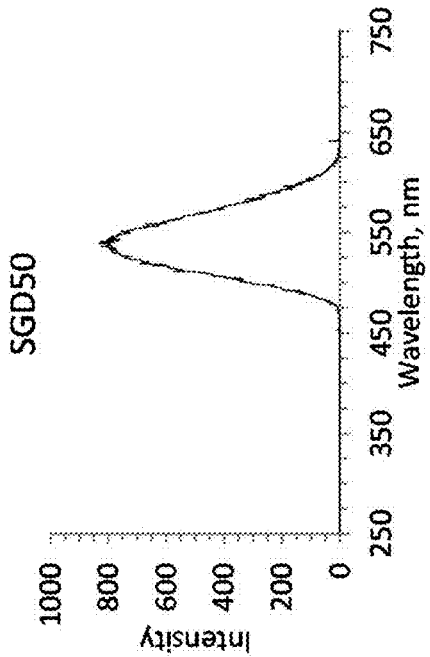
Figure 11A:
FIG. 11A is an image of a Singaporean banknote and FIG. 11B is a graph authenticated by SACOS with unique spectral fingerprints of the Singapore banknote.
Figure 11B:
Figure 12B:
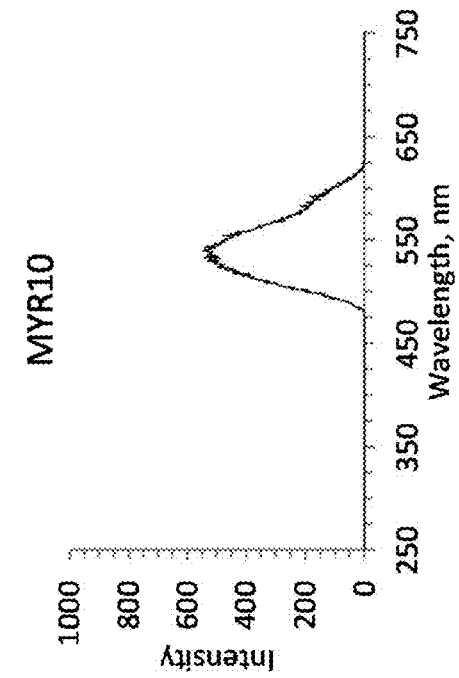
FIG. 12A is an image of a Swiss banknote and FIG. 12B is a graph authenticated by SACOS with unique spectral fingerprints of the Switzerland banknote.
Figure 12A:
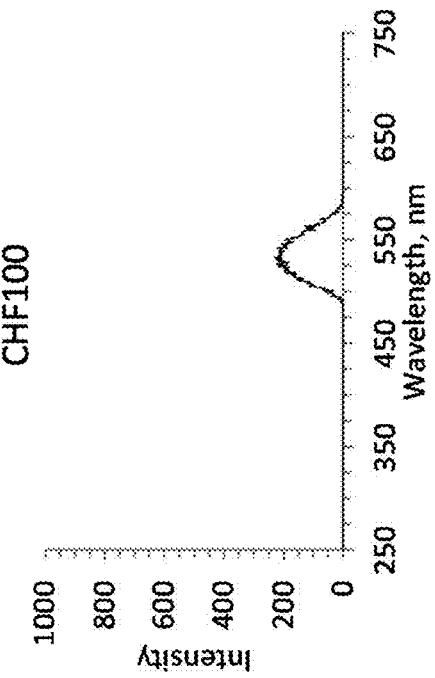
Figure 13B:
FIG. 13A is an image of a Malaysian banknote and FIG. 13B is a graph authenticated by SACOS with unique spectral fingerprints of the Malaysia banknote.
Figure 13A:
Figure 14A:
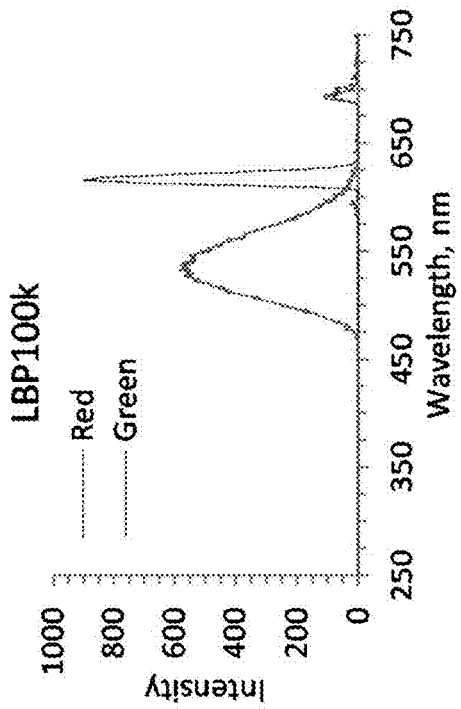
FIG. 14A is an image of a Lebanese banknote and FIG. 14B is a graph authenticated by SACOS with unique spectral fingerprints of the Lebanon banknote.
Figure 14B:
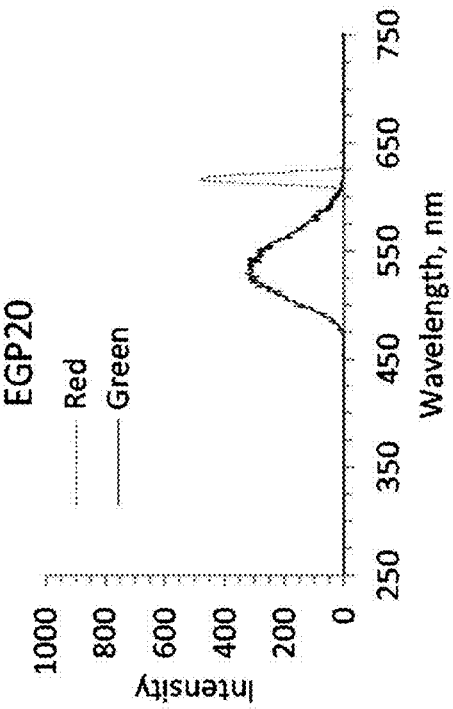
Figure 15A:
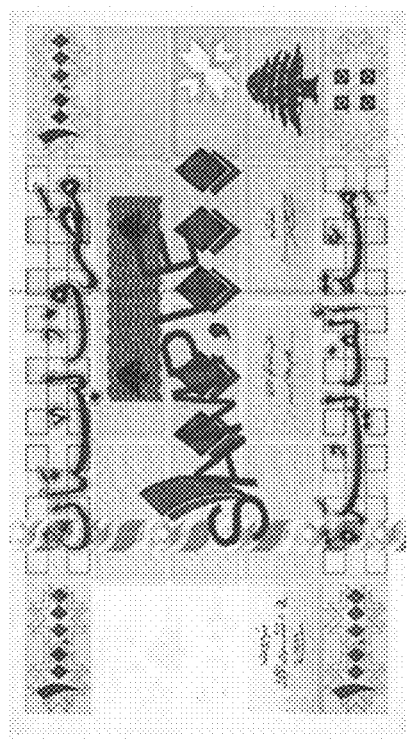
FIG. 15A is an image of an Egyptian banknote and FIG. 15B is a graph authenticated by SACOS with unique spectral fingerprints of the Egypt banknote.
Figure 15B:
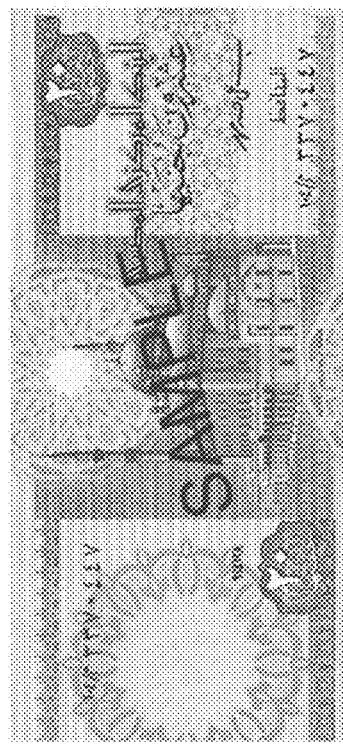
Figure 20B:
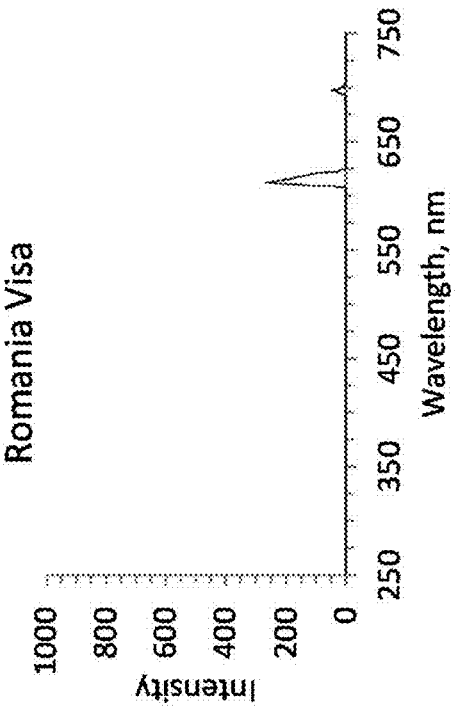
FIG. 20A is an image of a Romanian Visa and FIG. 20B is a graph authenticated by SACOS with unique spectral fingerprint of the Romania Visa.
Figure 21B:
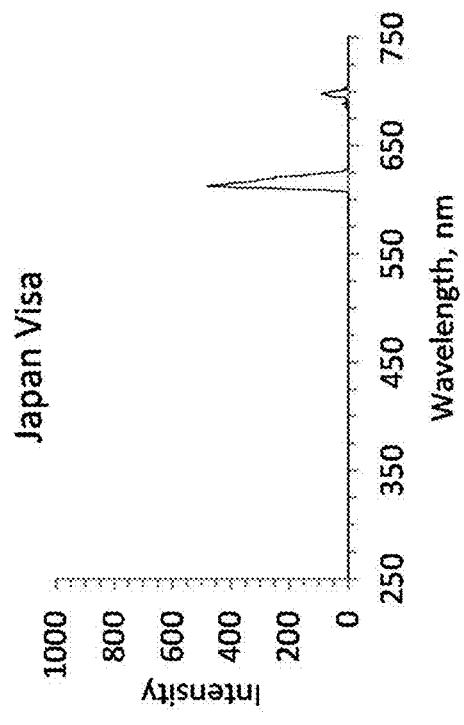
FIG. 21A is an image of a Japanese Visa and FIG. 21B is a graph authenticated by SACOS with unique spectral fingerprint of the Japan Visa.
Figure 20A:
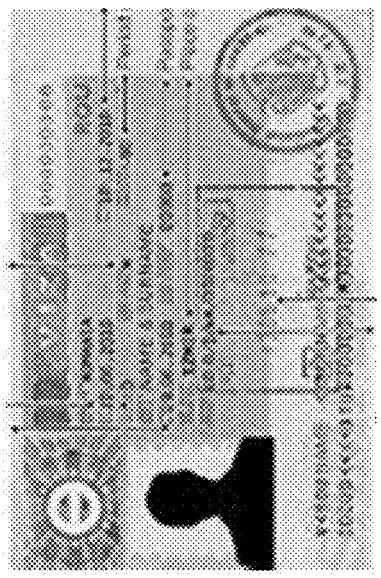
Figure 21A:
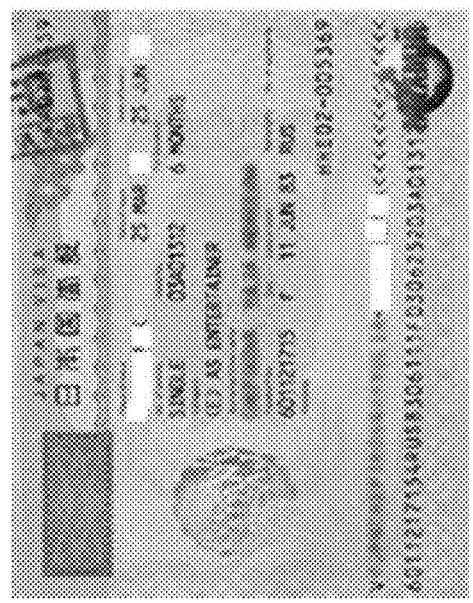
Figures 22A, 22B:
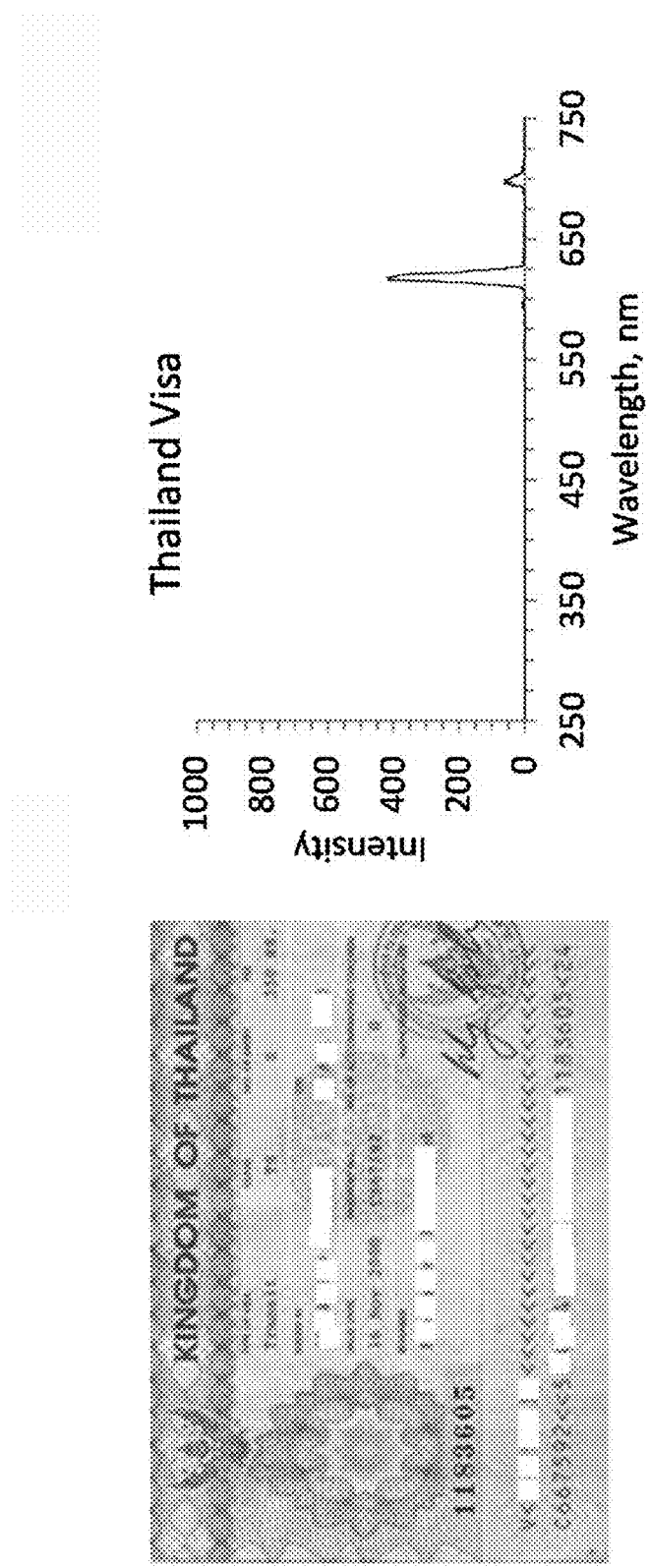
FIG. 22A is an image of a Thai Visa and FIG. 22B is a graph authenticated by SACOS with unique spectral fingerprint of the Thailand Visa.

Additional data is provided in FIGS. 4-21 for banknotes and passports/visas. FIGS. 4-15 tables provide the emission spectra of banknotes and FIGS. 16-21 provide emission spectra of passport/visas. It can be noticed from the emission spectra that some countries utilize the same material in their banknotes. For example, as shown in FIGS. 4-6, Bahraini banknotes (BHD), Iraqi banknotes (IQD), and Qatari banknotes (QAR), utilize the same material with multi-peak spectra whereas Great Britain banknotes (GBP), Indian banknotes (INR), and United States banknotes (USD) utilizes a material that has a single-peak spectra. It can also be noticed that trends are the same for emission spectra of different banknotes which can be explain by the use of a mixture of dyes (with fixed or different proportion) and that such banknotes are manufactured at the same factory. Some currencies utilize 2 different colors (Red and Green) of detectable ink such as Lebanon (LBP), Eygpt (EGP), and Thailand (THB) as seen in its spectra in FIGS. 14-16.

The development of the SACOS is combining cutting edge technologies in terms of organic dyes used as well as sensing system able to analyze optical signal within a lifetime of several microseconds which has always been considered as a challenge for spectroscopic measurements. The design of the SACOS is done in a way to respond to the need of banknotes and printing industries so as to make it portable instead of the actual bulky and non-accurate machines.

The SACOS method is mainly based on the combination of a new emission process and phosphorescence emission lifetime which is unique for each organic molecule. In addition, the phosphorescence emission occurs at longer wavelength and might also be seen at the borderline of the Vis/Infrared region so as making the new security features totally blinded to people who are mimicking authentic documents through counterfeiting or copying. Therefore, detection of faked documents becomes easier and more certain.

The invention has hitherto been described with reference to a SACOS method and apparatus that is used for checking banknotes and sorting them in accordance with the check. However, it is obvious that the invention can be used wherever banknotes must be judged with regard to their authenticity, e.g. also in vending machines, cash deposit machines, cash deposit and dispensing machines, so-called recyclers, etc. The SACOS method and apparatus may also be driven on mobile devices, such as through a hand held computer or smartphone (Apple®, Android®) upon development of a special application on Google Play Store or Apple Store.

The SACOS apparatus can be used as standalone apparatus for many end users. The SACOS apparatus can be miniaturized to be incorporated in machines existing at security check points e.g. counterfeit detectors. The SACOS apparatus will be able to read security features such as embedded inks.

It can be clearly shown from FIGS. 23A-23D that the unique phosphorescence fingerprint that was generated by SACOS can clearly discriminate between fake and authentic documents. The combination of intensity amplitude (z-axis), the phosphorescence spectrum (x-axis), and the decay (y-axis) provides a solid counterfeiting measure.

When analyzed, the intensity amplitude of the maximum phosphorescence peaks of the authentic EUR200 (@618 nm) is 8× more than the fake (@616 nm). The phosphorescence fingerprints are also characterized by several discrepancies that can be pointed out when looking at FIGS. 23A-23D such as several peaks that have long decay that are only available in the fake banknote and not in the authentic one. This indicated that the secure spot (FIG. 24A) used for the authentic EUR200 note is made of a chemical species having different properties than the one used by counterfeiters (FIG. 24B). Only SACOS can distinguish among them.

Terminology used herein is for the purpose of describing particular embodiments only and is not intended to be limiting of the invention. For example, as used herein, the singular forms "a", "an," and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal," and the like are used herein for the purpose of explanation only unless specifically indicated otherwise.

All references cited herein are incorporated by reference in their entireties.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of a Smart Anti-Counterfeiting Optical System—SACOS—comprising:
    a. optically measuring a specific substance on an official note or security paper selected from the group consisting of: Banknot, Passport, Visa, Bank Cheque, Driver License, and identification cards;
    b. detecting a polychromatic signal of a room temperature phosphorescence fingerprint, wherein the room temperature phosphorescence fingerprint is a combination of: wavelength, lifetime (decay), and amplitude oft the phosphorescence signal; and
    c. (1) comparing a plurality of count peaks exceeding a predefined threshold against a predefined database, biasing at least one capacitor above a predefined threshold, allowing the conversion of phosphorescence photons into a plurality electron charges at a semiconductor-oxide interface;
        (2) providing a relative scheme that includes a plurality of parameters for comparing ratios of a plurality of maximum emission peaks and decay time in seconds;
        (3) providing an advanced scheme that uses an Artificial Neural Network (ANN) for recognizing a measured spectrum for the detected polychromatic signal, accounting for a partially distorted spectra and reducing a false positives probability by the advanced scheme; and
        (4) using a decay of the room temperature phosphorescence of the specific substance to discriminate between different dyes used in the security paper or official note by a life time scheme.

2. The method of claim 1, wherein the optically measuring step further comprises an optical source that is a monochromatic or polychromatic light source.

3. The method of claim 2, further providing a micron core for excitation at about 1700 micron and a micron core for emission is about 50 microns.

4. The method of claim 3, further providing two layers of optical fibers include a first layer of 47 optical fibers and a second layer of 46 optical fibers in the rectangular shape guaranteed to deliver maximum signal collection.

5. The method of claim 4, further providing the proximal end of the second optical fiber operably coupled to a connector that is operably coupled to the detector.

6. The method of claim 5, further providing a detector selected from the group consisting of a CCD and a CMOS.

7. The method of claim 6, further providing an excitation signal as a monochromatic or a polychromatic signal including wavelengths from about 190 to 1100 nm.

8. The method of claim 7, further providing a phosphorescence signal emitted from the document to the detector that takes the form of a rectangular slit and is matched with the active zone of the detector to maximize the spectrometer throughput.

9. The method of claim 8, wherein the fingerprint corresponds to the emission spectra for the intensity and wavelength as shown in FIGS. 3-22 for the respective official note displayed therein.

10. The method of claim 9, further providing the two columns as a first column includes including at least 15 optical fibers and a second column includes including at least 16 optical fibers.

11. A method of authenticating documents comprising:
    a. comparing the unique room temperature phosphorescence fingerprint of the document to be tested according to the method of claim 1 against a predefined database; displaying a sample fingerprint in an accompanied figure; and
    b. using an Artificial Neural Network (ANN) for recognizing the measured spectrum to account for partially distorted spectra and to reduce the probability of false positives.

12. The method of claim 11, further comprising:
    a. comparing the ratios of the detected peaks.

13. The method of claim 12, using an additional AI technique.

14. The method of claim 13, further comprising:
    a. using the decay rate of the phosphorescence of the material to discriminate between the different dyes used in the documents.

* * * * *

UNITED STATES PATENT AND TRADEMARK OFFICE
CERTIFICATE OF CORRECTION

PATENT NO. : 10,354,469 B2
APPLICATION NO. : 15/582295
DATED : July 16, 2019
INVENTOR(S) : Antoine Ghauch and Ali Ammouri Page 1 of 1

It is certified that error appears in the above-identified patent and that said Letters Patent is hereby corrected as shown below:

In the Claims

Column 11, Line 37 Claim 1: "oft" should be changed to --of--.

Column 12, Lines 33 and 34 Claim 10: Please delete text "including".

Signed and Sealed this
Seventeenth Day of September, 2019

Andrei Iancu
*Director of the United States Patent and Trademark Office*